US012788262B2

(12) United States Patent
Huang et al.

(10) Patent No.: US 12,788,262 B2
(45) Date of Patent: Nov. 10, 2026

(54) PRESSURIZATION CONTROL METHOD FOR BLOOD PRESSURE MEASUREMENT AND BLOOD PRESSURE MEASUREMENT DEVICE USING THE SAME

(71) Applicant: AVITA Corporation, New Taipei City (TW)

(72) Inventors: Jui-Yang Huang, New Taipei City (TW); Wen-Jie Wu, New Taipei City (TW); I-Chih Huang, New Taipei City (TW)

(73) Assignee: AVITA Corporation, New Taipei City (TW)

( * ) Notice: Subject to any disclaimer, the term of this patent is extended or adjusted under 35 U.S.C. 154(b) by 516 days.

(21) Appl. No.: 18/227,309

(22) Filed: Jul. 28, 2023

(65) Prior Publication Data

US 2024/0065562 A1 Feb. 29, 2024

(30) Foreign Application Priority Data

Aug. 30, 2022 (TW) ................................. 111132749

(51) Int. Cl.
*A61B 5/0225* (2006.01)

(52) U.S. Cl.
CPC .... *A61B 5/0225* (2013.01); *A61B 2562/0247* (2013.01)

(58) Field of Classification Search
CPC .......... A61B 5/0225; A61B 2562/0247; A61B 5/02141; A61B 5/02225; A61B 5/0235
USPC .................................................. 600/490–499
See application file for complete search history.

(56) References Cited

U.S. PATENT DOCUMENTS

| | | | | |
|---|---|---|---|---|
| 4,889,132 A * | 12/1989 | Hutcheson ......... | A61B 5/02208 600/496 |
| 6,093,152 A * | 7/2000 | Patterson ............. | A61B 5/0225 600/490 |
| 6,719,702 B2 | 4/2004 | Lee et al. | |
| 2010/0292586 A1* | 11/2010 | Rooke .................. | A61B 5/0225 600/492 |
| 2011/0152650 A1 | 6/2011 | Donehoo et al. | |

(Continued)

FOREIGN PATENT DOCUMENTS

| | | | |
|---|---|---|---|
| CN | 1394546 A | 2/2003 | |
| CN | 108065925 A * | 5/2018 | ............ F04B 49/065 |

(Continued)

OTHER PUBLICATIONS

English Translation of CN 113827211A (Year: 2021).*

*Primary Examiner* — Navin Natnithithadha
(74) *Attorney, Agent, or Firm* — Che-Yang Chen

(57) ABSTRACT

A pressurization control method for blood pressure measurement is applied on a blood pressure measurement device, and includes connecting an airbag unit with a pump, a slow exhaust valve unit and a pressure sensor, wherein the slow exhaust valve unit has a nonlinear depressurization rate; controlling the pump to pressurize the airbag unit with a nonlinear inflation rate until pulses of a pressure signal outputted from the pressure sensor is interpreted to obtain a blood pressure measurement result, wherein the pump inflates the airbag unit with an inflation rate increasing nonlinearly upon a temporal sequence, and the slow exhaust valve unit depressurizes the airbag unit with a nonlinear depressurization rate upon the temporal sequence.

13 Claims, 6 Drawing Sheets

(56) References Cited

U.S. PATENT DOCUMENTS

| | | | | |
|---|---|---|---|---|
| 2016/0220195 | A1* | 8/2016 | Abu-Tarif | ............ A61B 5/7278 |
| 2018/0132732 | A1* | 5/2018 | Lin | ......................... F04B 35/04 |
| 2019/0099092 | A1 | 4/2019 | Zhang et al. | |
| 2020/0367770 | A1* | 11/2020 | Lin | .................... A61B 5/02233 |

FOREIGN PATENT DOCUMENTS

| | | | | | |
|---|---|---|---|---|---|
| CN | 111265201 | | | 6/2020 | |
| CN | 113827211 | A | * | 12/2021 | ............... A61B 5/72 |
| CN | 117898690 | A | * | 4/2024 | ............. A61B 5/681 |
| EP | 4331478 | A1 | * | 3/2024 | ........... A61B 5/0225 |
| JP | 6105814 | A | | 4/1994 | |
| JP | 10137204 | A | | 5/1998 | |
| JP | 2007130050 | A | | 5/2007 | |
| JP | 2021078552 | A | | 5/2021 | |
| JP | 2024035108 | A | * | 3/2024 | ........... A61B 5/0225 |
| TW | 200635559 | | | 10/2006 | |
| TW | 201632139 | | | 9/2016 | |
| TW | 202408418 | A | * | 3/2024 | ........... A61B 5/0225 |
| WO | WO-8603114 | A1 | * | 6/1986 | ......... A61B 5/02208 |
| WO | WO-2008050786 | A1 | * | 5/2008 | ............. A61B 5/022 |
| WO | WO2017206838 | | | 12/2017 | |
| WO | 2018135553 | A1 | | 7/2018 | |

* cited by examiner

PRESSURIZATION CONTROL METHOD FOR BLOOD PRESSURE MEASUREMENT AND BLOOD PRESSURE MEASUREMENT DEVICE USING THE SAME

BACKGROUND OF THE INVENTION

1. Field of the Invention

The present invention relates to a blood pressure measurement device and the pressurization control method, more particularly to a pressurization control method for blood pressure measurement and a blood pressure measurement device using the same.

2. Description of the Related Art

High blood pressure is a chronic disease that is common but easily overlooked in Chinese people. Therefore, a blood pressure measurement device is a common blood pressure detection device for families with elderly elders. A conventional blood pressure measurement device needs to control a pump to perform linear inflation for blood pressure measurement. The most commonly used means of linear inflation control is the feedback control method, which detects the pressure regularly through a pressure sensor and limits the speed of pump inflation within a certain inflation rate to eliminate deviations, so as to obtain an expected system performance, as shown in FIG. 1, which is a flowchart of a pressurization control method for a conventional blood pressure measurement device with a low-startup-voltage pump.

However, the above-mentioned conventional blood pressure measurement device requires a very low startup voltage for the pump, and requires the reduction of inflation rate during the inflation process not to cause noise interference due to the voltage drop being too low at the moment the pump is stopped and then started again. Therefore, the above-mentioned conventional blood pressure measurement device can only inflate the air bag by using a low-startup-voltage pump in the feedback control mode, and cannot be provided with a slow exhaust valve to measure a blood pressure result. The above-mentioned blood pressure measurement device controls the low-startup-voltage pump to inflate the air bag via a pulse width modulation (PWM) signal during pressurization and inflation, and continuously captures a current pressure and pulses through a pressure sensor. When the difference between the current pressure and the previous pressure is less than a lower limit, the low-startup-voltage pump is controlled to increase an inflation rate; when the difference between the current pressure and the previous pressure is greater than an upper limit, the low-startup-voltage pump is controlled to decrease the inflation rate. Therefore, during the pressurization and inflation period of the above-mentioned conventional blood pressure measurement device, the air bag can perform the linear pressurization (such as the line L1 shown in FIG. 2) until a blood pressure measurement result including diastolic pressure, average pressure, systolic pressure is obtained based on the captured current pressure and its pulse waveform, such as L2 shown in FIG. 2.

When the conventional blood pressure measurement device uses a high startup voltage pump to shorten the pressurization and inflation time for obtaining blood pressure measurement result, the conventional blood pressure measurement device measures the pulse waveform by the feedback control method, as shown in FIG. 3. However, this conventional blood pressure measurement device causes the pump to stop and restart during the pressurization and inflation period, resulting in the pressure falling and then rising again (such as the inflation and pressurization line L1 marked by a frame shown in FIG. 3), and resulting in the pulse wave interference (such as a line L2 shown in FIG. 3).

Therefore, in order to prevent the noise interference problem caused at the moment the pump stops and restarts, and the present invention provides a pressurization control method for blood pressure measurement and a blood pressure measurement device using the same, and the technical solution of the present invention has higher industrial utilization.

SUMMARY OF THE INVENTION

An objective of the present invention is to provide a pressurization control method for blood pressure measurement, the pressurization control method adopts a nonlinear increasing inflation rate and a slow exhaust valve having a nonlinear decreasing depressurization, to achieve linear inflation control.

In order to achieve the above-mentioned objective, the present invention provides a pressurization control method for blood pressure measurement, wherein the pressurization control method is applied on a blood pressure measurement device and includes: connecting an airbag unit with a pump and a pressure sensor; controlling the pump to perform pressurization on the airbag unit with a nonlinear inflation rate until a pulse of a pressure signal outputted from the pressure sensor is interpreted to obtain a blood pressure measurement result.

According to an embodiment of the present invention, the pressurization control method further includes: connecting the airbag unit with a slow exhaust valve unit, wherein the slow exhaust valve unit has a nonlinear depressurization rate.

According to an embodiment of the present invention, the step of controlling the pump with a nonlinear inflation rate further includes: controlling the pump via a pulse width modulation (PWM) signal, wherein the PWM has an adjustable duty cycle; linearly increasing a duty cycle of the PWM signal upon a temporal sequence, to inflate the airbag unit with the nonlinear inflation rate, wherein the slow exhaust valve unit depressurizes the airbag unit with a nonlinear depressurization rate upon the temporal sequence.

In order to achieve the above-mentioned objective, the present invention provides a blood pressure measurement device, include an airbag unit, a pump, a pressure sensor and a processing unit, the airbag unit is connected with the pump and the pressure sensor, and the processing unit is configured to control the pump with a nonlinear inflation rate; when performing pressurization on the airbag unit, the processing unit interprets pulses of a pressure signal outputted from the pressure sensor, to obtain a blood pressure measurement result.

According to an embodiment of the present invention, the processing unit is configured to control the pump with a PWM signal, and the PWM signal has an adjustable duty cycle, and the processing unit linearly increases a duty cycle of the PWM signal upon a temporal sequence.

According to the above-mentioned pressurization control method for blood pressure measurement and the blood pressure measurement device using the same, the present invention can adopt a high-startup-voltage pump or a low-startup-voltage pump during pressurization and inflation, the method and the blood pressure measurement device of the present invention can prevent the noise interference caused at the moment the pump stops and then restarts, and can achieve linear inflation control.

BRIEF DESCRIPTION OF THE DRAWINGS

The structure, operating principle and effects of the present invention will be described in detail by way of various embodiments which are illustrated in the accompanying drawings.

DETAILED DESCRIPTION OF THE PREFERRED EMBODIMENTS

Figure 1:
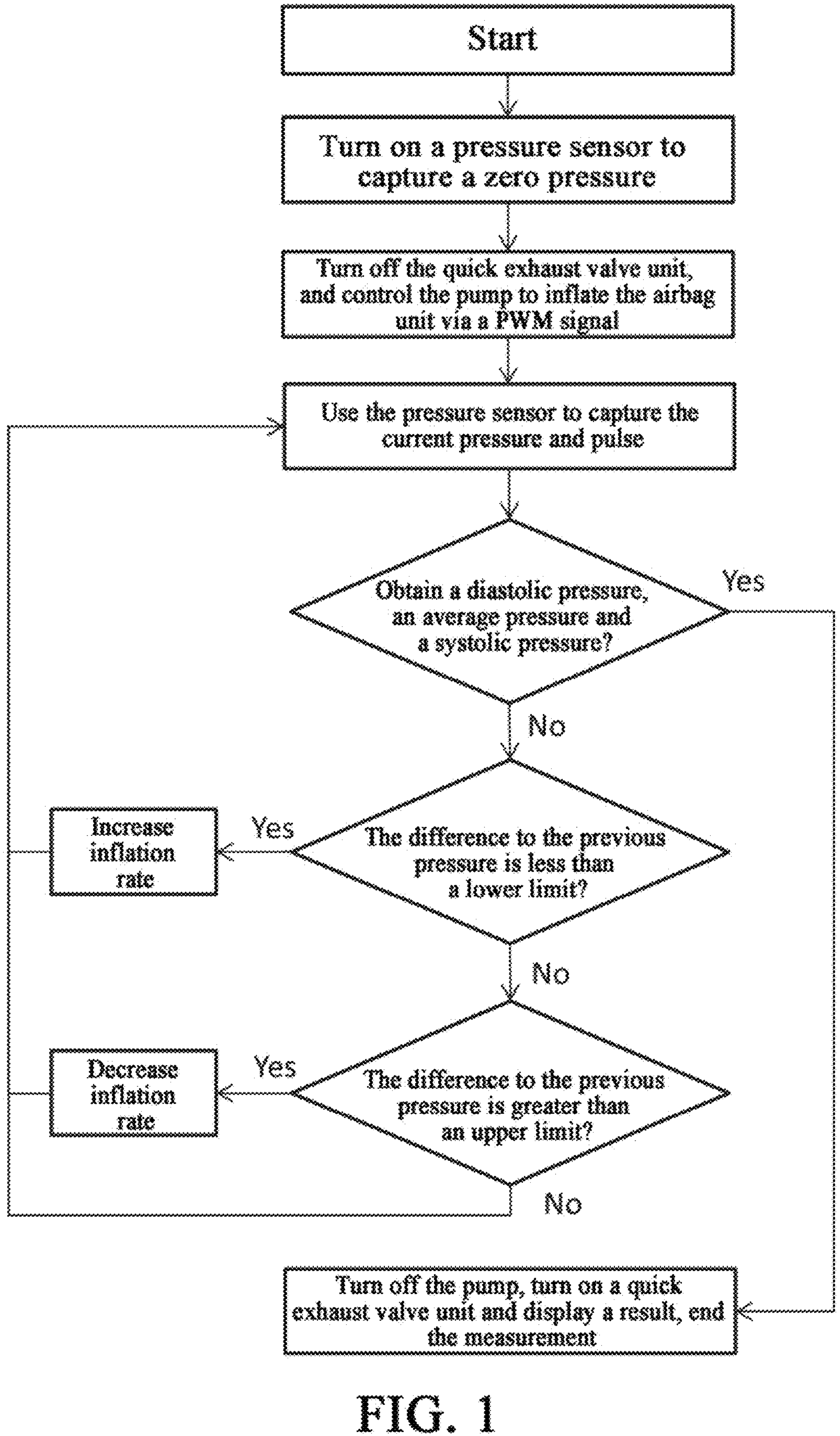
FIG. 1 is a flowchart of a pressurization control method adopting a low startup voltage pump in prior art.
Figure 2:
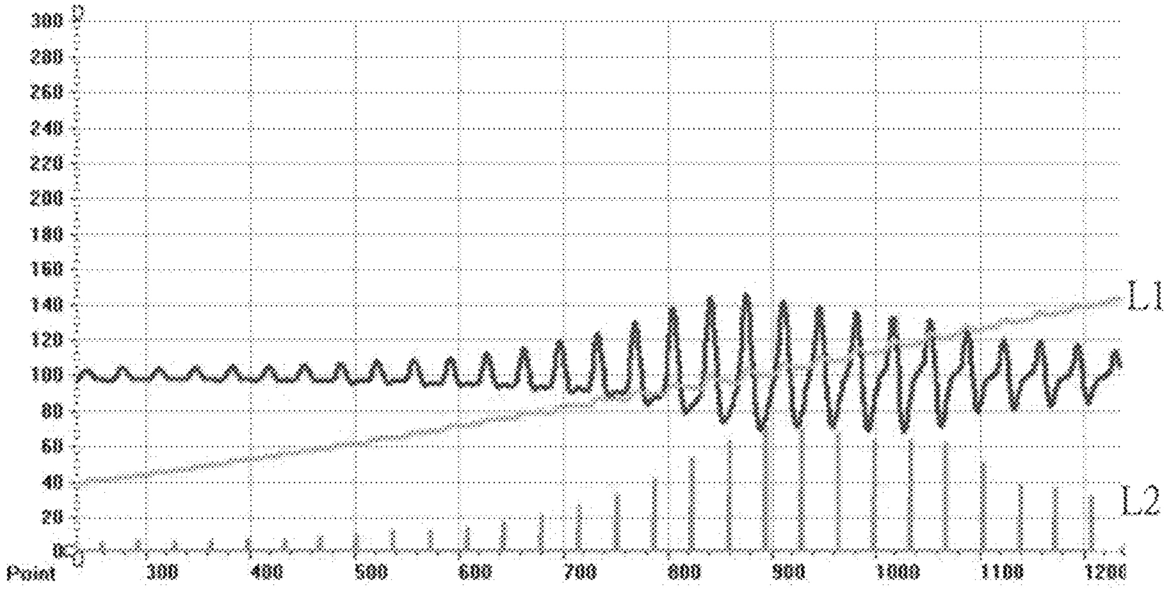
FIG. 2 is a waveform diagram of a pressure signal, pulses and linear pressurization inflation measured in the pressurization control method of FIG. 1.

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims.

These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts. As used herein, the singular forms "a", "an" and "the" are intended to include the plural forms as well, unless the context clearly indicates otherwise.

It is to be acknowledged that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the words "comprise" and "include", and variations such as "comprises", "comprising", "includes", or "including", will be acknowledged to imply the inclusion of stated elements but not the exclusion of any other elements.

Figure 4:
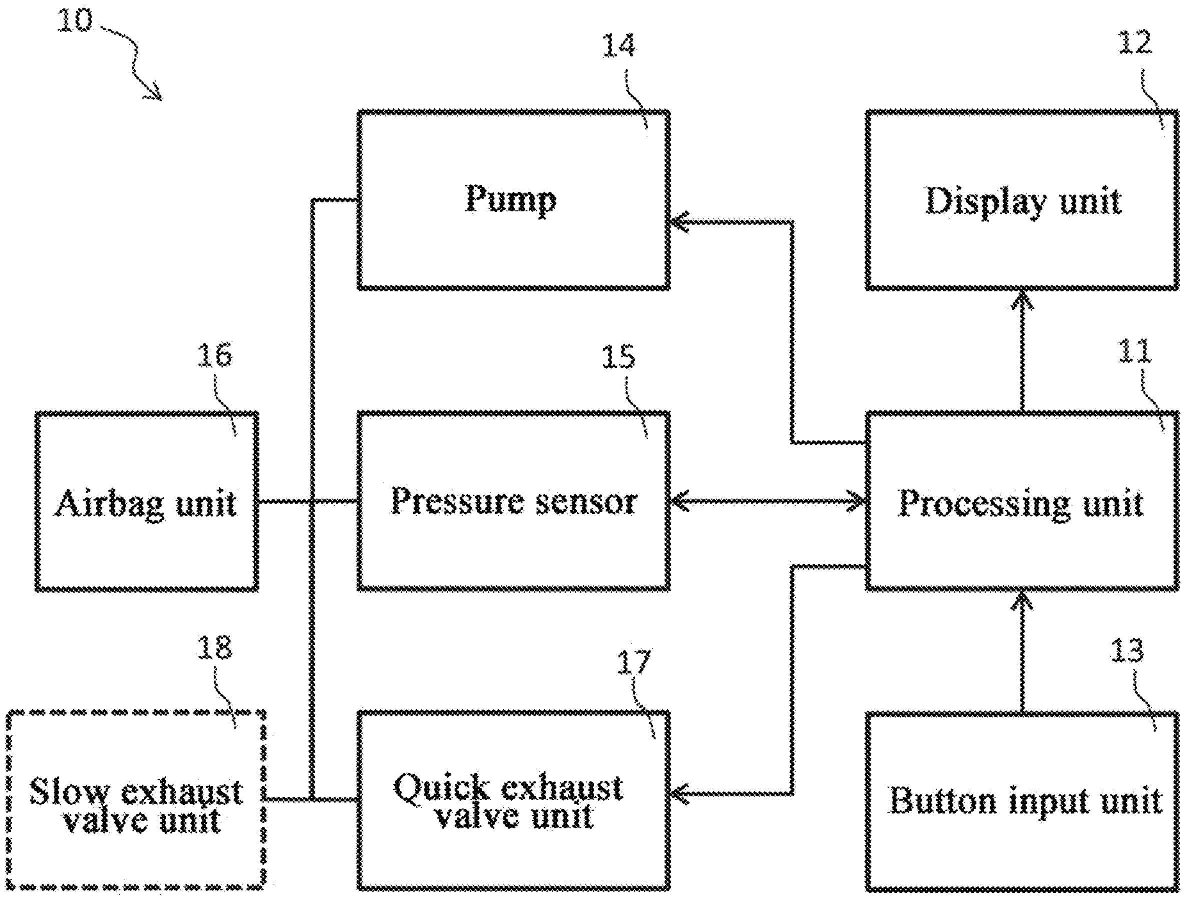
FIG. 4 is a system block diagram of a blood pressure measurement device, according to the present invention.

Please refer to FIG. 4, which is a system block diagram of a blood pressure measurement device, according to the present invention. In a first embodiment of the present invention, a blood pressure measurement device 10 mainly includes a processing unit 11, a display unit 12, a button input unit 13, a pump 14, a pressure sensor 15, an airbag unit 16, a quick exhaust valve unit 17 and a power supply unit (not shown in FIG. 1). The power supply unit is configured to provide electrical power to component units of the blood pressure measurement device 10. The airbag unit 16 can be a cuff airbag unit, the airbag unit 16 is connected with the pump 14, the quick exhaust valve unit 17, and the pressure sensor 15. The display unit 12 can be a LCD device. The button input unit 13 is configured to provide a user to start a blood pressure measurement mode of the blood pressure measurement device. The processing unit 11 includes a storage unit configured to store a program instruction set, and the processing unit 11 executes the program instruction set to execute the pressurization control method for blood pressure measurement, according to the present invention.

Figure 5:
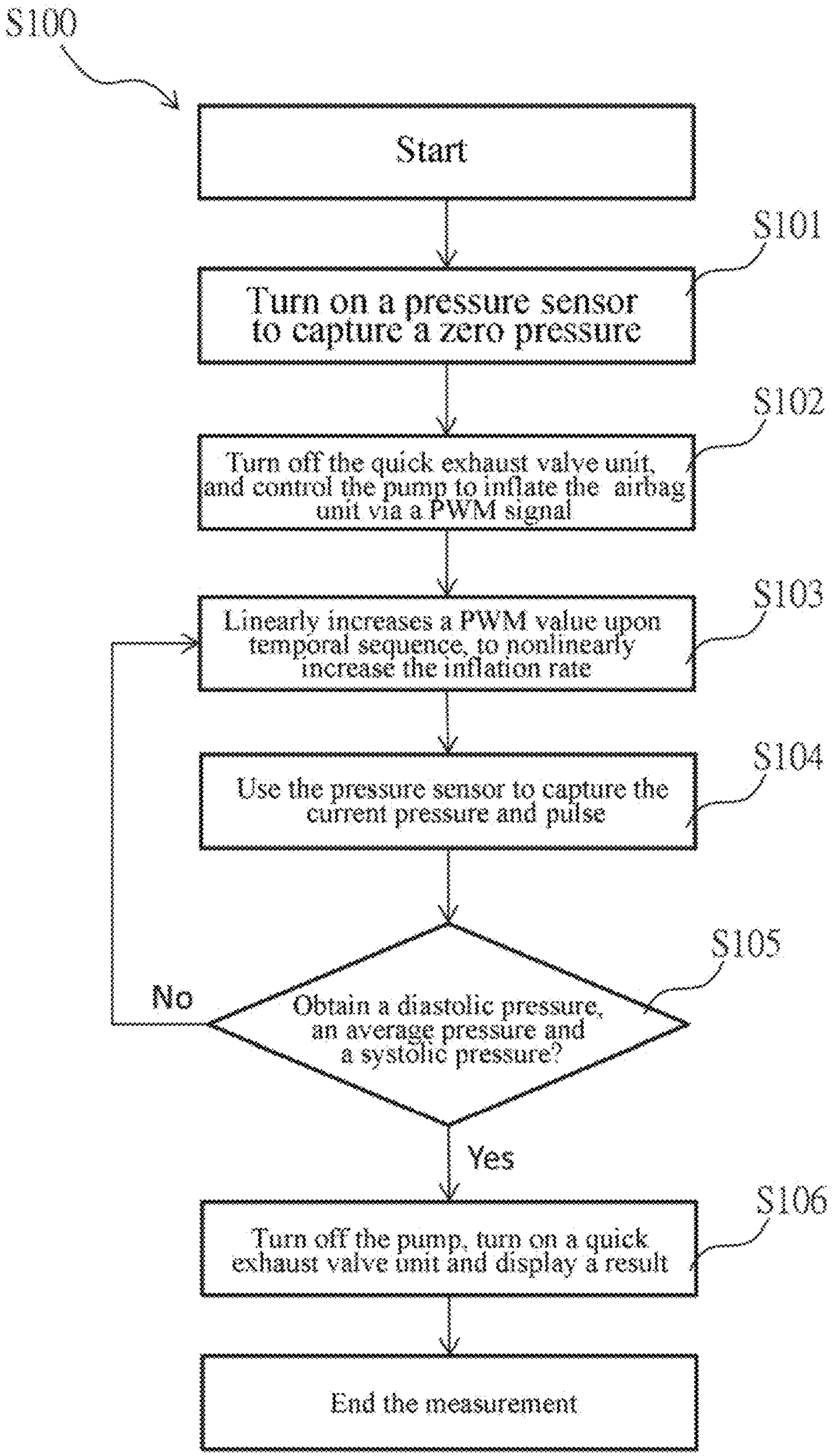
FIG. 5 is a flowchart of a pressurization control method for blood pressure measurement, according to the present invention.

Please refer to FIG. 5, which is a flowchart of a pressurization control method for blood pressure measurement, according to the present invention. In a first embodiment of the present invention, the blood pressure measurement device 10 does not include a slow exhaust valve unit 18, and adopts a high-startup-voltage pump 14 to perform nonlinear increasing inflation rate on the airbag unit 16 in a feedback control manner. Therefore, when the quick exhaust valve unit 17 is turned off, the processing unit 11 captures a current pressure value through pressure sensor 15; the current pressure value is a value of pressure applied on the airbag unit 16 to inflate with a current inflation rate by the pump 14. After the user operates the button input unit 13 to start the blood pressure measurement mode of the blood pressure measurement device, the processing unit 11 executes the following steps of the pressurization control method for blood pressure measurement, according to the present invention.

Figure 6:
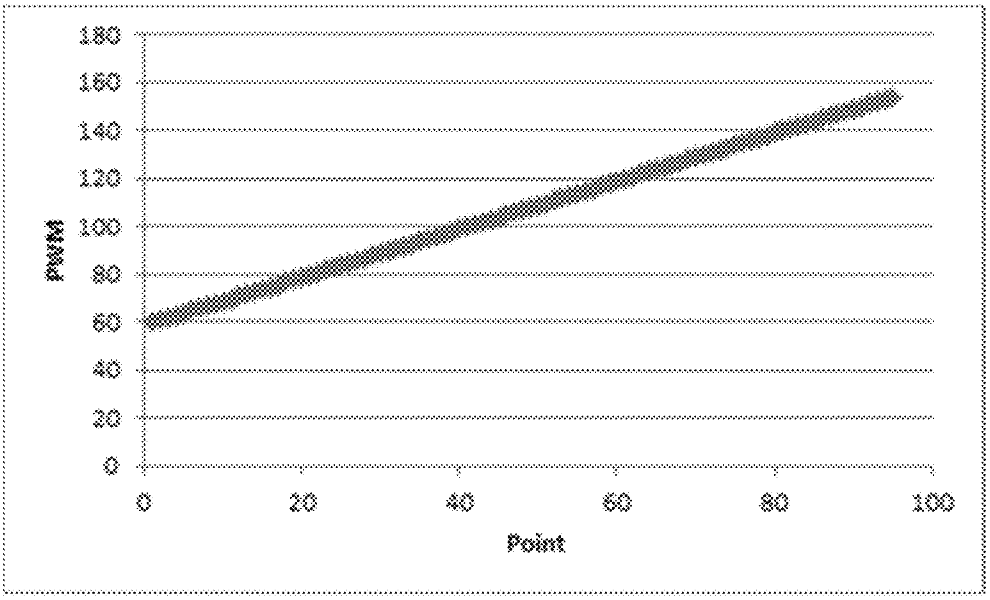
FIG. 6 is a schematic view of a linear increasing value of PWM signal, according to the present invention.
Figure 7:
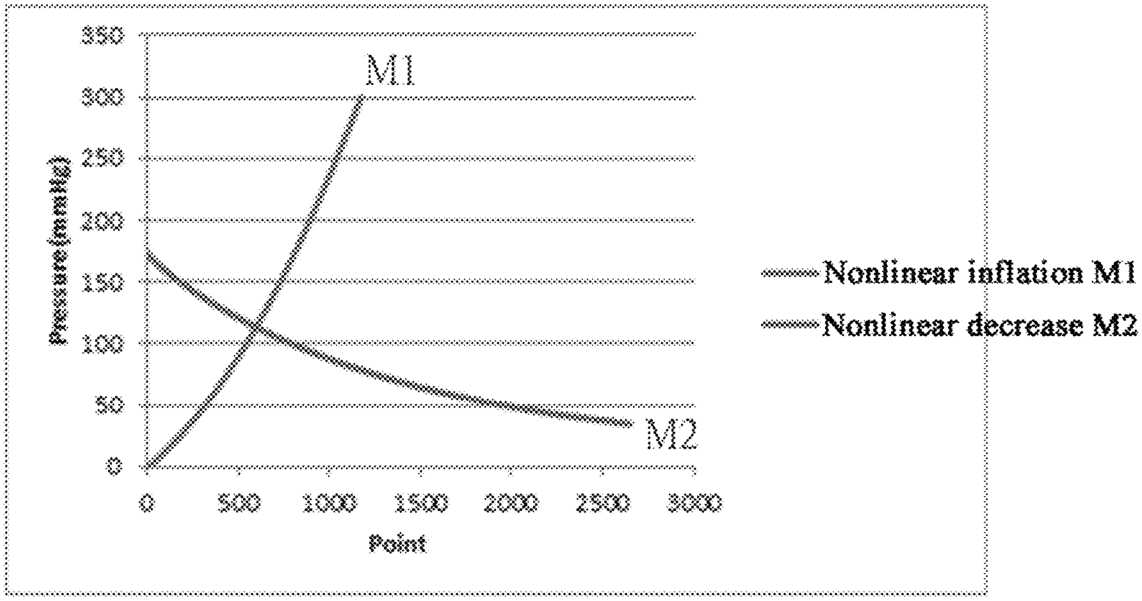
FIG. 7 is a schematic view of a nonlinear increasing inflation rate of a pump and a nonlinear decreasing depressurization of a slow exhaust valve unit controlled upon temporal sequence.

In a step 101, the processing unit 11 turns on the pressure sensor 15 to capture the zero pressure of the airbag unit 16. In a step S102 the processing unit 11 turns off the quick exhaust valve unit 17, and controls the pump 14 to inflate the airbag unit 16 via a PWM signal. In a step S103, the processing unit 11 linearly increases a PWM value to control the pump 14 upon temporal sequence, to make the pump 14 increasingly inflate the airbag unit 16 nonlinearly. Please refer to FIG. 6, which shows a schematic view of a linear increasing PWM value according to the present invention. The PWM value corresponds to a duty cycle controlled by the PWM signal, the different PWM value corresponds to different duty cycle. The processing unit 11 applies different PWM value to control the pump 14 to inflation the airbag unit 16 with a different inflation rate. As shown in FIG. 6, upon a temporal sequence, the PWM value is increased linearly over time, to increase the inflation rate of the pump 14 over time to make pressurization faster, such as the line M1 with a nonlinear increasing value in FIG. 7. Therefore, the processing unit 11 can control the pump 14 to inflate the airbag unit 16 with a nonlinear increasing inflation rate.

When performing pressurization on the airbag unit 16, the processing unit 11 continuously executes a step S104. The processing unit 11 captures the current pressure of the airbag unit 16 through the pressure sensor 15, and interpret the pulse waveform based on the pressure signal outputted from the pressure sensor 15. Next, the processing unit 11 continuously executes a step S105, the processing unit 11 determines whether the blood pressure measurement result including a diastolic pressure, an average pressure and a systolic pressure are obtained based on the waveform and amplitude of the pulses. When the processing unit 11 determines that the blood pressure measurement result is not obtained yet, the processing unit 11 repeats the step S103, to inflate the airbag unit 16 with the nonlinear increasing inflation rate until the processing unit 11 obtains the blood pressure measurement result including the diastolic pressure, the average pressure and the systolic pressure in the step S105.

After obtaining the blood pressure measurement result, the processing unit 11 executes a step S106 to turn off the pump 14, turn on the quick exhaust valve unit 17 to quickly exhaust the airbag unit 16, and display the blood pressure measurement result including diastolic pressure, average pressure, and systolic pressure on the display unit 12.

Figure 3:
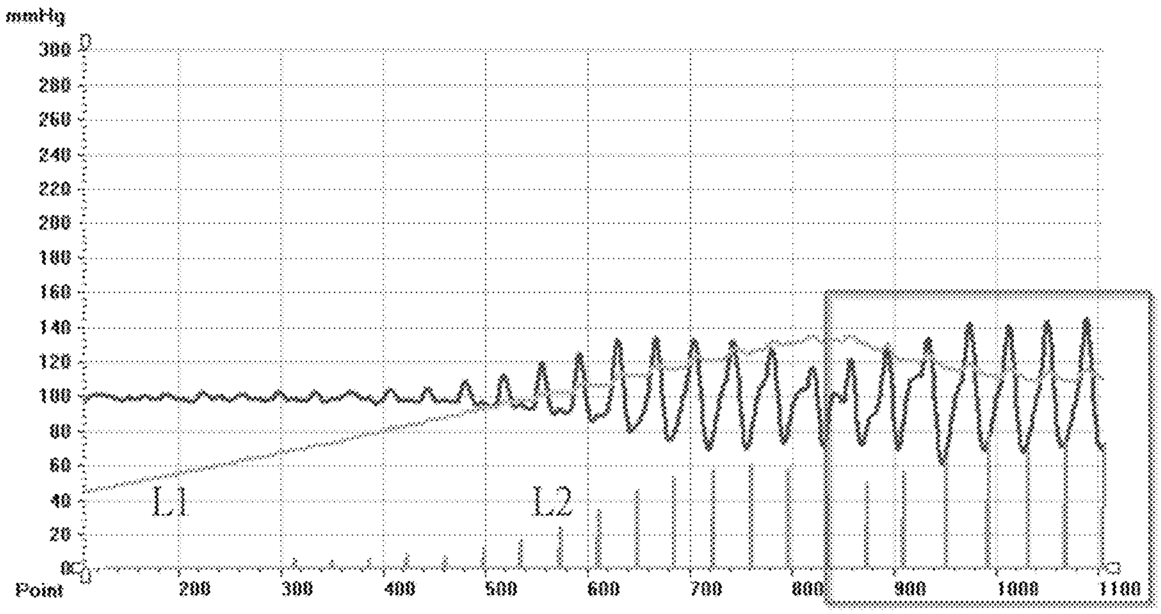
FIG. 3 is a waveform diagram of a pressure signal, pulses and pressurization inflation measured by conventional technology adopting a high-startup-voltage pump.
Figure 8:
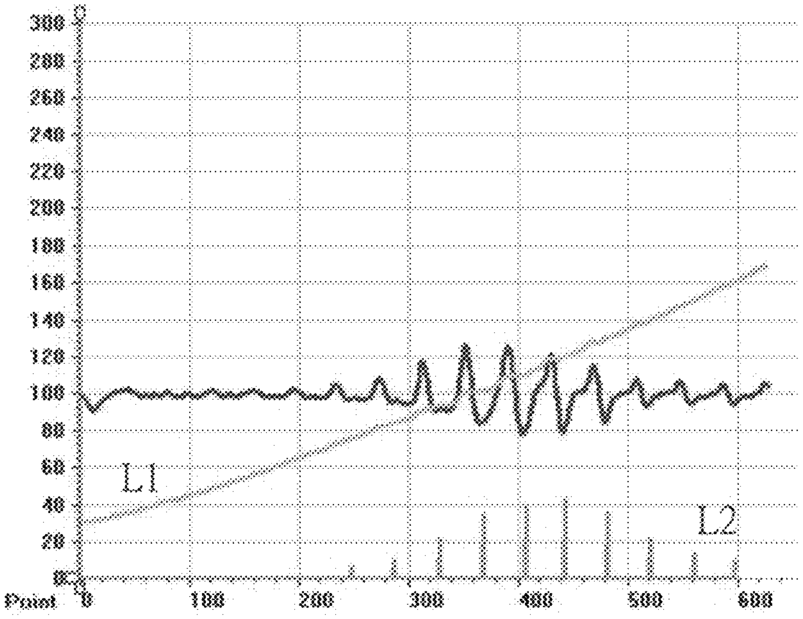
FIG. 8 is a waveform diagram of a pressure signal, pulses and nonlinear pressurization inflation measured by a first embodiment of the present invention.

Please refer to FIG. 8, which is a waveform diagram of a pressure signal, pulses, and nonlinear pressurization inflation measured by a first embodiment of the present invention. In a first embodiment of the present invention, the blood pressure measurement device 10 adopts the high-startup-voltage pump 14 to control the airbag unit 16 with a nonlinear increasing inflation rate in a feedback control manner, such as the inflation pressurization line L1 shown in FIG. 8. The blood pressure measurement device 10 of the present invention does not make the pump stop and then restart during pressurization inflation, to prevent pulse noise interference because the pressure drops and then rises, such as the inflation pressurization line L1 shown in FIG. 3. The first embodiment of the present invention solves the problem caused by the pump which is stopped and then restarted, but causes the problem that the sampling rate is insufficient due to too fast inflation and may result in inaccurate data calculation. The present invention further provides a second embodiment of the blood pressure measurement device 10, to solve the problem of the first embodiment having an insufficient sampling rate.

Please refer to FIG. 4, which is a system block diagram of a blood pressure measurement device, according to the present invention. In the second embodiment of the present invention, the blood pressure measurement device 10 further includes a slow exhaust valve unit 18, the airbag unit 16 is connected with the pump 14, the quick exhaust valve unit 17, the slow exhaust valve unit 18, and the pressure sensor 15. The slow exhaust valve unit 18 has a nonlinear depressurization rate. The line M2 shown in FIG. 7 has a nonlinear decreasing rate, the slow exhaust valve unit 18 depressurizes the airbag unit 16 with a nonlinear depressurization rate upon the temporal sequence. When the pressure of the airbag unit 16 is higher, the depressurization rate of the slow exhaust valve unit 18 is higher; when the pressure of the airbag unit 16 is lower, the depressurization rate of the slow exhaust valve unit 18 is lower.

Figure 9:
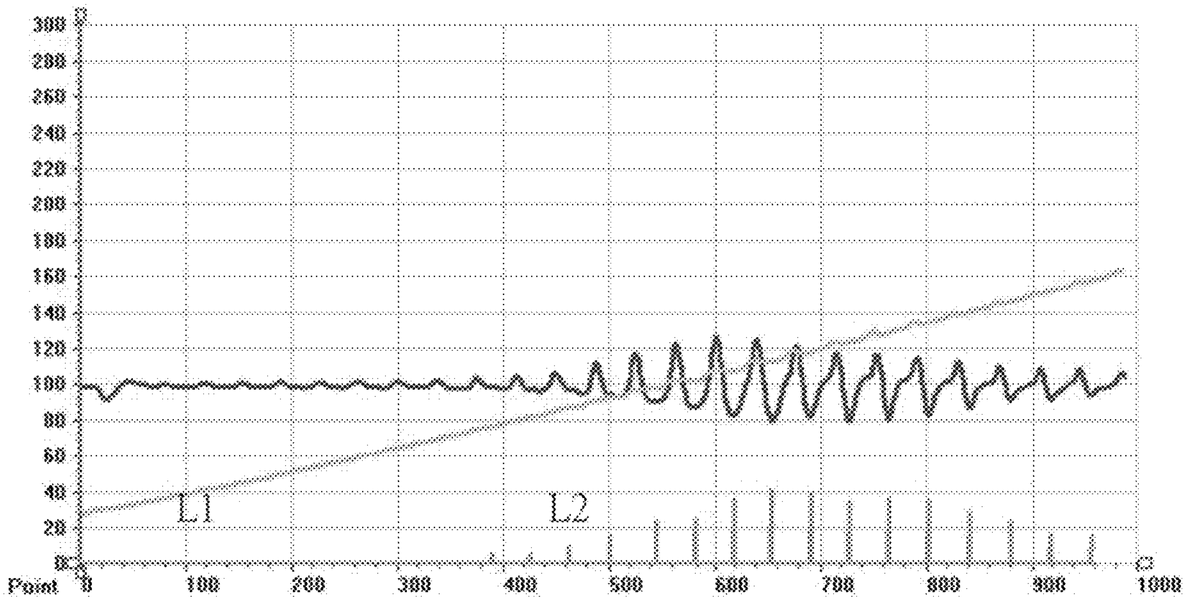
FIG. 9 is a waveform diagram of a pressure signal, pulses and linear pressurization inflation measure by a second embodiment of the present invention.

In the second embodiment of the present invention, after the user operates the button input unit 13 to start a blood pressure measurement mode of the blood pressure measurement device, the processing unit 11 similarly executes the steps of the pressurization control method shown in FIG. 5. The steps can refer to the above-mentioned content, so the details are not repeated herein. The difference between the first embodiment and the second embodiment is that the pressurization effects applied on the airbag unit 16 are different. In the second embodiment of the present invention, the blood pressure measurement device 10 can adopt any one of the high-startup-voltage pump 14 and the low-startup-voltage pump 14 to control the airbag unit 16 with nonlinear increasing inflation rate in the feedback control manner; during inflation pressurization, the slow exhaust valve unit 18 is adopted to depressurize the airbag unit 16 with a nonlinear depressurization rate upon a temporal sequence, so that the second embodiment can make the airbag unit 16 have linear pressurization effect, as shown in FIG. 9, which shows a waveform diagram of a pressure signal, pulses and linear pressurization inflation measured by the second embodiment. In the second embodiment of the present invention, the blood pressure measurement device 10 does not make the pump stop and then restart, so as to prevent the pressure from dropping and then rising again to cause pulse noise interference, and the linear pressurization effect does not cause the problem that the sampling rate is insufficient and results in inaccurate data calculation.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A pressurization control method for blood pressure measurement, wherein the pressurization control method is applied on a blood pressure measurement device and comprises:

connecting an airbag unit with a pump and a pressure sensor;

controlling, using a processing unit, the pump to perform pressurization on the airbag unit with a nonlinear inflation rate, wherein during the pressurization with the nonlinear inflation rate, interpreting a pulse of a pressure signal outputted from the pressure sensor to obtain a blood pressure measurement result; and controlling, using the processing unit, the pump via a pulse width modulation (PWM) signal, wherein the PWM has an adjustable duty cycle, and linearly increasing the adjustable duty cycle of the PWM signal upon a temporal sequence.

2. The pressurization control method according to claim 1, further comprising:

connecting the airbag unit with a slow exhaust valve unit, wherein the slow exhaust valve unit has a nonlinear depressurization rate.

3. The pressurization control method according to claim 2, wherein the pump inflates the airbag unit with the nonlinear inflation rate upon a temporal sequence, and the slow exhaust valve unit depressurizes the airbag unit with the nonlinear depressurization rate upon the temporal sequence.

4. The pressurization control method according to claim 1, wherein the airbag unit performs a quasi-linear pressurization process upon the temporal sequence.

5. The pressurization control method according to claim 4, wherein when an internal pressure of the airbag unit is higher, the nonlinear depressurization rate of the slow exhaust valve unit is higher, and when the internal pressure of the airbag unit is lower, the nonlinear depressurization rate of the slow exhaust valve unit is lower.

6. The pressurization control method according to claim 1, further comprising:

connecting the airbag unit with a quick exhaust valve unit; and after the blood pressure measurement result is obtained, turning on the quick exhaust valve unit to quickly depressurize the airbag unit.

7. A blood pressure measurement device, comprising:

a pump;

a pressure sensor;

an airbag, connected with the pump and the pressure sensor; and a processing unit, configured to control the pump to perform pressurization on the airbag unit with a nonlinear inflation rate, wherein during the pressurization with the nonlinear inflation rate, the processing unit interprets a pulse of a pressure signal outputted from the pressure sensor to obtain a blood pressure measurement result;

wherein the processing unit controls the pump via a pulse width modulation (PWM) signal, wherein the PWM has an adjustable duty cycle, and the processing unit linearly increases the adjustable duty cycle of the PWM signal upon a temporal sequence.

8. The blood pressure measurement device according to claim 7, wherein the airbag unit is connected with a slow exhaust valve unit, and the slow exhaust valve unit has a nonlinear depressurization rate.

9. The blood pressure measurement device according to claim 7, wherein the pump inflates the airbag unit with the nonlinear inflation rate upon a temporal sequence, and the slow exhaust valve unit depressurizes the airbag unit with the nonlinear depressurization rate upon the temporal sequence.

10. The blood pressure measurement device according to claim 7, wherein the airbag unit performs a quasi-linear pressurization process upon the temporal sequence.

11. The blood pressure measurement device according to claim 10, wherein when an internal pressure of the airbag unit is higher, the nonlinear depressurization rate of the slow exhaust valve unit is higher, and when the internal pressure of the airbag unit is lower, the nonlinear depressurization rate of the slow exhaust valve unit is lower.

12. The blood pressure measurement device according to claim 7, wherein the airbag unit is connected with a quick exhaust valve unit, and after the blood pressure measurement result is obtained, the quick exhaust valve unit is turned on to quickly depressurize the airbag unit.

13. The blood pressure measurement device according to claim 7, wherein the processing unit interprets the pulses of the pressure signal outputted from the pressure sensor, to obtain the blood pressure measurement result, and displays the blood pressure measurement result on a display unit.

* * * * *